(12) United States Patent
Chapelon et al.

(10) Patent No.: US 7,497,858 B2
(45) Date of Patent: Mar. 3, 2009

(54) APPARATUS AND METHOD FOR ASSESSING TRANSMURALITY OF A TISSUE ABLATION

(75) Inventors: Pierre-Antoine Chapelon, Carrieres sur Seine (FR); Dany Berube, Milpitas, CA (US); Hiep Nguyen, Milpitas, CA (US); Faouzi Kallel, Fremont, CA (US)

(73) Assignee: Maquet Cardiovascular LLC, San Jose, CA (US)

( * ) Notice: Subject to any disclaimer, the term of this patent is extended or adjusted under 35 U.S.C. 154(b) by 0 days.

(21) Appl. No.: 11/682,744

(22) Filed: Mar. 6, 2007

(65) Prior Publication Data

US 2007/0149967 A1 Jun. 28, 2007

Related U.S. Application Data

(63) Continuation of application No. 10/369,887, filed on Feb. 19, 2003, now Pat. No. 7,192,427.

(60) Provisional application No. 60/358,215, filed on Feb. 19, 2002.

(51) Int. Cl.
*A61B 18/18* (2006.01)
(52) U.S. Cl. .............................. 606/33; 606/41; 600/547
(58) Field of Classification Search .................... 606/33
See application file for complete search history.

(56) References Cited

U.S. PATENT DOCUMENTS

| | | | |
|---|---|---|---|
| 4,641,649 A | 2/1987 | Walinsky et al. |
| 5,246,438 A | 9/1993 | Langberg |
| 5,314,466 A | 5/1994 | Stern et al. |
| 5,403,312 A | 4/1995 | Yates et al. |
| 5,405,346 A | 4/1995 | Grundy et al. |
| 6,245,062 B1 | 6/2001 | Berube et al. |
| 6,287,302 B1 | 9/2001 | Berube |
| 6,312,427 B1 | 11/2001 | Berube et al. |
| 6,322,558 B1 | 11/2001 | Taylor et al. |

(Continued)

FOREIGN PATENT DOCUMENTS

WO WO 01/58373 A1 8/2001

OTHER PUBLICATIONS

James L. Cox MD et al, *The surgical treatment of atrial fibrillation*, Journal of Thoracic and Cardiovascular Surgery, Apr. 1991, pp. 402-426, 569-592, vol. 101, No. 4.

(Continued)

*Primary Examiner*—Lee S Cohen
(74) *Attorney, Agent, or Firm*—Fenwick & West LLP

(57) ABSTRACT

An instrument assesses the transmurality of an ablation lesion from a first surface of a targeted biological tissue to an opposed second surface thereof. The instrument includes at least a first electrode operably attached to an ablation instrument adapted to engage a tissue first surface, and at least a second electrode adapted to engage a tissue second surface, the at least second electrode positioned generally opposed to the at least first electrode. Alternatively, the at least second electrode may be adapted to be placed within a chamber of an organ. These electrodes facilitate measuring at least one of conduction time, conduction velocity, phase angle, and impedance through at least a portion of the targeted tissue to determine the transmurality of the ablation lesion.

8 Claims, 8 Drawing Sheets

U.S. PATENT DOCUMENTS

| | | |
|---|---|---|
| 6,546,935 B2 | 4/2003 | Hooven |
| 6,663,622 B1 * | 12/2003 | Foley et al. .................. 606/34 |
| 6,740,080 B2 * | 5/2004 | Jain et al. .................... 606/34 |
| 6,743,225 B2 * | 6/2004 | Sanchez et al. .............. 606/34 |
| 6,761,716 B2 * | 7/2004 | Kadhiresan et al. .......... 606/34 |
| 6,802,840 B2 * | 10/2004 | Chin et al. ................... 606/41 |
| 7,033,352 B1 | 4/2006 | Gauthier et al. |
| 2002/0087151 A1 * | 7/2002 | Mody et al. .................. 606/15 |
| 2003/0004507 A1 * | 1/2003 | Francischelli et al. ........ 606/41 |

OTHER PUBLICATIONS

David E. Haines et al, *Tissue Healing During Radiofrequency Catheter Ablation: A Thermodynamic Model and Observations in Isolated Perfused and Superfused Canine Right Ventricular Free Wall*, Pacing and Clinical Electrophysiology, Jun. 1989, pp. 962-976, vol. 12, No. 6.

* cited by examiner

APPARATUS AND METHOD FOR ASSESSING TRANSMURALITY OF A TISSUE ABLATION

RELATED APPLICATION

This application claims the benefit under 35 U.S.C. § 120 as a continuation of U.S. patent. application Ser. No. 10/369,887, filed Feb. 19, 2003, now U.S. Pat. No. 7,192,427, which claims priority under 35 U.S.C. § 120 to U.S. Provisional Application Ser. No. 60/358,215, filed Feb. 19, 2002, entitled TRANSMURALITY ASSESSMENT DEVICE, which applications are incorporated herein in their entireties by this reference thereto to form a part hereof.

FIELD OF INVENTION

This invention relates to tissue ablation instruments and lesion formations, and more particularly to apparatus and method for assessing tissue ablation transmurality.

BACKGROUND OF THE INVENTION

It is well documented that atrial fibrillation, either alone or as a consequence of other cardiac disease, continues to persist as the most common cardiac arrhythmia. According to recent estimates, more than two million people in the U.S. suffer from this common arrhythmia, roughly 0.15% to 1.0% of the population. Moreover, the prevalence of this cardiac disease increases with age, affecting nearly 8% to 17% of those over 60 years of age.

Atrial arrhythmia may be treated using several methods. Pharmacological treatment of atrial fibrillation, for example, is initially the preferred approach, first to maintain normal sinus rhythm, or secondly to decrease the ventricular response rate. Other forms of treatment include drug therapies, electrical cardioversion, and RF catheter ablation of selected areas determined by mapping. In the more recent past, other surgical procedures have been developed for atrial fibrillation, including left atrial isolation, transvenous catheter or cryosurgical ablation of His bundle, and the Corridor procedure, which have effectively eliminated irregular ventricular rhythm. However, these procedures have for the most part failed to restore normal cardiac hemodynamics, or alleviate the patient's vulnerability to thromboembolism because the atria are allowed to continue to fibrillate. Accordingly, a more effective surgical treatment was required to cure medically refractory atrial fibrillation of the Heart.

On the basis of electrophysiologic mapping of the atria and identification of macroreentrant circuits, a surgical approach was developed which effectively creates an electrical maze in the atrium (i.e., the MAZE procedure) and precludes the ability of the atria to fibrillate. Briefly, in the procedure commonly referred to as the MAZE III procedure, strategic atrial incisions are performed to prevent atrial reentry circuits and allow sinus impulses to activate the entire atrial myocardium, thereby preserving atrial transport function postoperatively. Since atrial fibrillation is characterized by the presence of multiple macroreentrant circuits that are fleeting in nature and can occur anywhere in the atria, it is prudent to interrupt all of the potential pathways for atrial macroreentrant circuits. These circuits, incidentally, have been identified by intraoperative mapping both experimentally and clinically in patients.

Generally, this procedure includes the excision of both atrial appendages, and the electrical isolation of the pulmonary veins. Further, strategically placed atrial incisions not only interrupt the conduction routes of the common reentrant circuits, but they also direct the sinus impulse from the sinoatrial node to the atrioventricular node along a specified route. In essence, the entire atrial myocardium, with the exception of the atrial appendages and the pulmonary veins, is electrically activated by providing for multiple blind alleys off the main conduction route between the sinoatrial node to the atrioventricular node. Atrial transport function is thus preserved postoperatively as generally set forth in the series of articles: Cox, Schuessler, Boineau, Canavan, Cain, Lindsay, Stone, Smith, Corr, Change, and D'Agostino, Jr., *The Surgical Treatment Atrial Fibrillation* (pts. 1-4), 101 THORAC CARDIOVASC SURG., 402-426, 569-592 (1991).

While this MAZE III procedure has proven effective in treating medically refractory atrial fibrillation and associated detrimental sequelae, this operational procedure is traumatic to the patient since this is an open-heart procedure and substantial incisions are introduced into the interior chambers of the Heart. Consequently, other techniques have been developed to interrupt atrial fibrillation restore sinus rhythm. One such technique is strategic ablation of the atrial tissues and lesion formation through tissue ablation instruments.

Most approved tissue ablation systems now utilize radio frequency (RF) energy as the ablating energy source. Accordingly, a variety of RF based catheters, medical instrument and power supplies are currently available to electrophysiologists. However, radio frequency energy has several limitations including the rapid dissipation of energy in surface tissues resulting in shallow "burns" and failure to access deeper arrhythmic tissues. Another limitation of RF ablation catheters is the risk of clot formation on the energy emitting electrodes. Such clots have an associated danger of causing potentially lethal strokes in the event that a clot is dislodged from the catheter. It is also very difficult to create continuous long lesions with RF ablation instruments.

As such, instruments which utilize other energy sources as the ablation energy source, for example in the microwave frequency range, are currently being developed. Microwave frequency energy, for example, has long been recognized as an effective energy source for heating biological tissues and has seen use in such hyperthermia applications as cancer treatment and preheating of blood prior to infusions. Accordingly, in view of the drawbacks of the traditional catheter ablation techniques, there has recently been a great deal of interest in using microwave energy as an ablation energy source. The advantage of microwave energy is that it is much easier to control and safer than direct current applications and it is capable of generating substantially larger and longer lesions than RF catheters, which greatly simplifies the actual ablation procedures. Such microwave ablation systems are described in the U.S. Pat. No. 4,641,649 to Walinsky; U.S. Pat. No. 5,246,438 to Langberg; U.S. Pat. No. 5,405,346 to Grundy, et al.; and U.S. Pat. No. 5,314,466 to Stern, et al, each of which is incorporated herein by reference.

Regardless of the energy source applied to ablate the arrhythmic tissues, these strategically placed lesions must electrically sever the targeted conduction paths. Thus, not only must the lesion be properly placed and sufficiently long, it must also be sufficiently deep to prevent the electrical impulses from traversing the lesion. Ablation lesions of insufficient depth may enable currents to pass over or under the lesion, and thus be incapable of disrupting, or otherwise interrupting, the reentry circuits. In most cases, accordingly, it is desirable for the ablation lesion to be transmural.

To effectively disrupt electrical conduction through the cardiac tissue the tissue temperature must reach a threshold where irreversible cellular damage occurs. The temperature at the margin between viable and nonviable tissue has been demonstrated to be about 48° C. to about 50° C. Haines et al. Haines D E, Watson D D, Tissue heating during radiofrequency catheter ablation: a thermodynamic model and observations in isolated perfused and superfused canine right ventricular free wall, Pacint Clin Electrophysiol, June 1989, 12(6), pp. 962-76.)

Thus, to ensure ablation, the tissue temperature should exceed this margin. This, however, is often difficult to perform and/or assess since the cardiac tissue thickness varies with location and, further, varies from one individual to another.

Most tissue ablation instruments typically ablate tissue through the application of thermal energy directed toward a targeted biological tissue, in most cases the surface of the biological tissue. As the targeted surface of the biological tissue heats, for example, the ablation lesion propagates from the targeted surface toward an opposed second surface of the tissue. Excessive thermal energy at the interface between the tissue and the ablation head, on the other hand, is detrimental as well. For example, particularly with RF energy applications, temperatures above about 100° C. can cause coagulation at the RF tip. Moreover, the tissue may adhere to the tip, resulting in tearing at the ablation site upon removal of the ablation instrument, or immediate or subsequent perforation may occur. Thin walled tissues are particularly susceptible.

Generally, if the parameters of the ablation instrument and energy output are held constant, the lesion size and depth should be directly proportional to the interface temperature and the time of ablation. However, the lag in thermal conduction of the tissue is a function of the tissue composition, the tissue depth and the temperature differential. Since these variables may change constantly during the ablation procedure, and without overheating the tissues at the interface, it is often difficult to estimate the interface temperature and time of ablation to effect a proper transmural ablation, especially with deeper arrhythmic tissues.

Several attempts have been made to assess the completion or transmurality of an ablation lesion. The effective disruption of the electrical conduction of the tissue does of course affect the electrical characteristics of the biological tissue. Thus, some devices and techniques have been developed which attempt to measure at least one of the electrical properties, such as those based upon a function of impedance (e.g., its value, the change in value, or the rate of change in value) of the ablated tissue, to determine whether the ablation is transmural and complete. Typical of these devices include U.S. Pat. No.: 6,322,558 to Taylor et al. and U.S. Pat. No. 5,403,312 to Yates et al.; U.S. patent application Ser. No. 09/747,609 to Hooven; and WIPO Pub. No. WO 01/58373 A1 to Foley et al., each of which is incorporated by reference in its entirety.

While these recent applications have been successful in part, they all tend to measure the electrical properties of the targeted ablation tissue directly from the surfaces of the tissue (i.e., the top surface or the underside surface of the tissue). This may be problematic since the measurement of such electrical properties can produce false indications with respect to transmurality of the ablation; a decrease in the change of impedance measured across the lesion indicative of transmurality, however, knowing there is insufficient energy applied to truly created a transmural lesion, as one example.

Accordingly, it would be advantageous to provide an apparatus and method to better assess the transmurality of an ablation lesion during an ablation procedure, for instance, by providing certain tissue characteristic measurements from one surface of a bodily organ or from two opposing surfaces or from one surface relative the blood pool. Furthermore, it would be advantageous to provide digital signal processing to the tissue measurement obtained in order to better assess the transmurality of a newly created ablation lesion.

SUMMARY OF THE INVENTION

The present invention provides a measurement accessory or instrument useful for facilitating tissue ablation procedures of sensitive biological tissue such as those of internal organs. In particular, the present invention is suitable for assessing the transmurality of an ablation lesion formed from a first surface of cardiac tissue of the heart to an opposed second surface thereof to electrically isolate conduction paths thereof during treatment of arrhythmia.

The measurement instrument may be part of an ablation system or an accessory thereto. The instrument or accessory includes at least a first sensor which is positioned proximate a first tissue surface, and at least a second sensor positioned proximate a second tissue surface. The first sensor is adapted to transmit a first signal. The second sensor is adapted to interpret a signal responsive to the first signal, the responsive signal being related to one or more tissue characteristics observed during the creation of an ablation lesion. These measurements can then be analyzed to determine the transmurality or effectiveness of the ablation procedure.

Accordingly, by collectively analyzing this measured data, a surgeon may gauge whether an ablation procedure has been properly performed. Unlike the current transmurality assessment procedures, the present invention is capable of conducting measurements through the means of very simple and straight forward purse string openings leading to the interior of the organ and placement of various sensors therein.

In one specific embodiment, the first and second sensors are electrodes to measure the electrical characteristics to measure at least one of conduction time, conduction velocity, phase angle, and impedance through at least a portion of the targeted tissue. Using this information, audio or visual feedback may be provided to determine the ablation transmurality, or other lesion characteristic. In other examples, the feedback information may be applied for automatic closed-loop control of the energy applied to the target tissue by a tissue ablation instrument.

In another embodiment, the second electrode is provided on the distal end of an elongated shaft placed within the interior of an organ, through a purse string opening for example. The second electrode, while perhaps not in direct contact with a tissue surface opposed to the first electrode, electrically communicates a signal responsive to the transmitted signal from the first electrode.

In another aspect of the present invention, a tissue ablation assembly is provided that is adapted to ablate a targeted biological tissue from a first surface thereof to an opposed second surface thereof to form an ablation lesion. The ablation assembly includes an elongated transmission line having a proximal portion suitable for connection to an energy source. An antenna assembly is coupled to the transmission line, and is adapted to transmit energy therefrom sufficiently strong to cause tissue ablation at the first surface. A manipulating device may be included which cooperates with the ablation assembly for manipulative movement thereof. A first sensor is further included and positioned within at least a portion of the ablative zone of the antenna assembly. The first sensor cooperates with a second sensor located proximate to a second tissue surface opposed to the first tissue surface. The second sensor is operatively attached to a needle member adapted to pierce the outer surface of the organ and advance to a point interior to the organ, proximate to the second tissue surface opposed to the first tissue surface.

In yet another aspect of the present invention, a method is provided for assessing the transmurality of an ablation lesion from a first surface of a targeted biological tissue to an opposed second surface thereof. The method includes placing a first sensor proximate a first surface of a target tissue and placing a second sensor proximate to a second opposing surface of the target tissue. Once the sensors are placed, a first signal is transmitted from the first sensor. The first signal propagates through at least a portion of the target tissue and a signal responsive to the first signal is received by the second sensor, the responsive signal being related to one or more of conduction time, conduction velocity, phase angle, and impedance through at least a portion of the targeted tissue, to determine the transmurality of the ablation lesion created or being created. The method further includes utilization of digital signal processing to better evaluate the measured responsive signal and, thus, better assess transmurality during or after the ablation lesion is being created.

Another method is included for forming a transmural lesion from a first surface of a targeted biological tissue to an opposed second surface thereof. The method includes manipulating an antenna assembly of an ablation instrument into engagement with or substantially adjacent to the tissue first surface, and generating an electromagnetic field from the antenna assembly sufficiently strong to cause tissue ablation to the tissue first surface. The antenna assembly includes at least a first electrode. The method further includes piercing a needle member, having an elongated shaft, into the targeted biological tissue from the tissue first surface. The needle member includes at least a second electrode, the second electrode being placed proximate a second tissue surface opposed to the antenna assembly placement. Transmitting and receiving electrical signals by and between the first and second electrodes is performed to measure at least one of conduction time, conduction velocity, phase angle, and impedance through a portion of the biological tissue.

In one specific configuration, the method includes engaging the second electrode with the tissue second surface. The piercing event includes driving the shaft into the organ, placing the second electrode in contact with the tissue second surface proximate to the ablation lesion during or after creation. In another specific configuration, the second electrode is placed with the bodily organ proximate to the tissue second surface. The piercing event includes driving the shaft into the organ, holding the second electrode suspended therein. Subsequently, the method includes measuring the at least one of conduction time, conduction velocity, phase angle, and impedance between the first and second electrodes.

In yet another aspect of the present, a method for treating medically refractory atrial fibrillation of the heart is provided. This method includes manipulating an antenna assembly of an ablation instrument into engagement with or substantially adjacent to a first surface of targeted cardiac tissue of the heart, and generating an electromagnetic field from the antenna assembly sufficiently strong to cause tissue ablation to the first surface to form an ablation lesion extending from the first surface toward an opposed second surface of the heart. The antenna assembly includes a first electrode attached thereto. In accordance with this aspect of the present invention, before, during or after generating, the method next includes piercing a needle member having an elongated shaft into cardiac tissue from the heart epicardial surface. The needle member includes at least a second electrode which is placed proximate to an endocardial surface of the heart. Next the method includes transmitting and receiving electrical signals to measure at least one of conduction time, conduction velocity, phase angle, and impedance through at least a portion of the targeted cardiac to determine the transmurality of the ablation lesion. The manipulating, generating, piercing and measuring events are repeated to form a plurality of strategically positioned ablation lesions and/or to divide the left and/or right atria to substantially prevent reentry circuits.

In one specific embodiment, the ablation lesions are strategically formed to create a predetermined conduction pathway between a sinoatrial node and an atrioventricular node of the heart. In another application, the manipulating, generating, piercing and measuring are repeated in a manner isolating the pulmonary veins from the epicardium of the heart.

BRIEF DESCRIPTION OF THE DRAWINGS

The assembly of the present invention has other objects and features of advantage which will be more readily apparent from the following description of the best mode of carrying out the invention and the appended claims, when taken in conjunction with the accompanying drawing, in which:

DETAILED DESCRIPTION OF THE INVENTION

Figure 1:
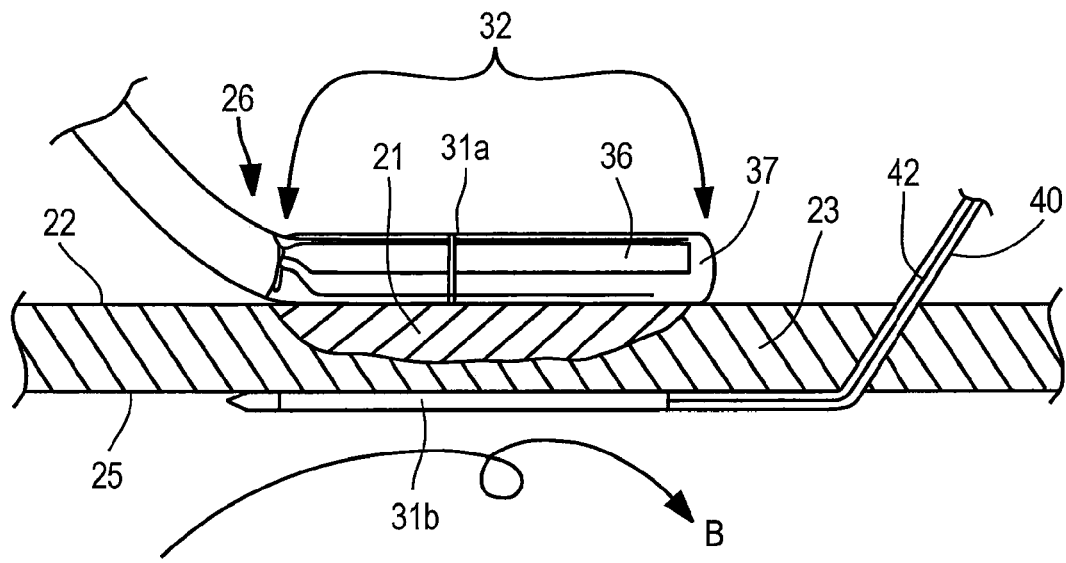
FIG. 1 is a fragmentary side elevation view, in cross-section, of a transmurality assessment instrument for assessing the transmurality of an ablation lesion in accordance with one embodiment of the present invention.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various Figures.

Figure 3:
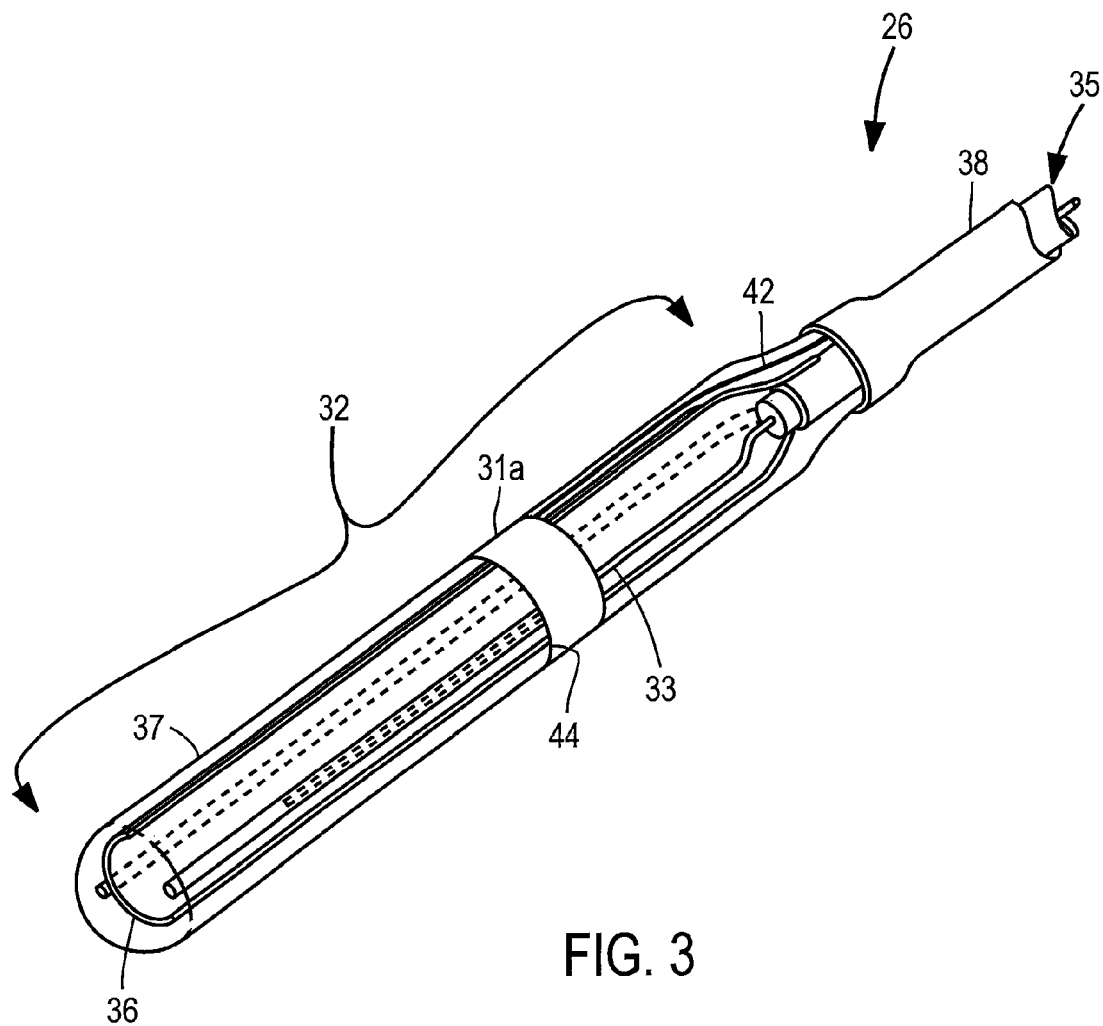
FIG. 3 is a fragmentary, top perspective view of an ablation assembly of an ablation instrument in accordance with the invention.
Figure 4A:
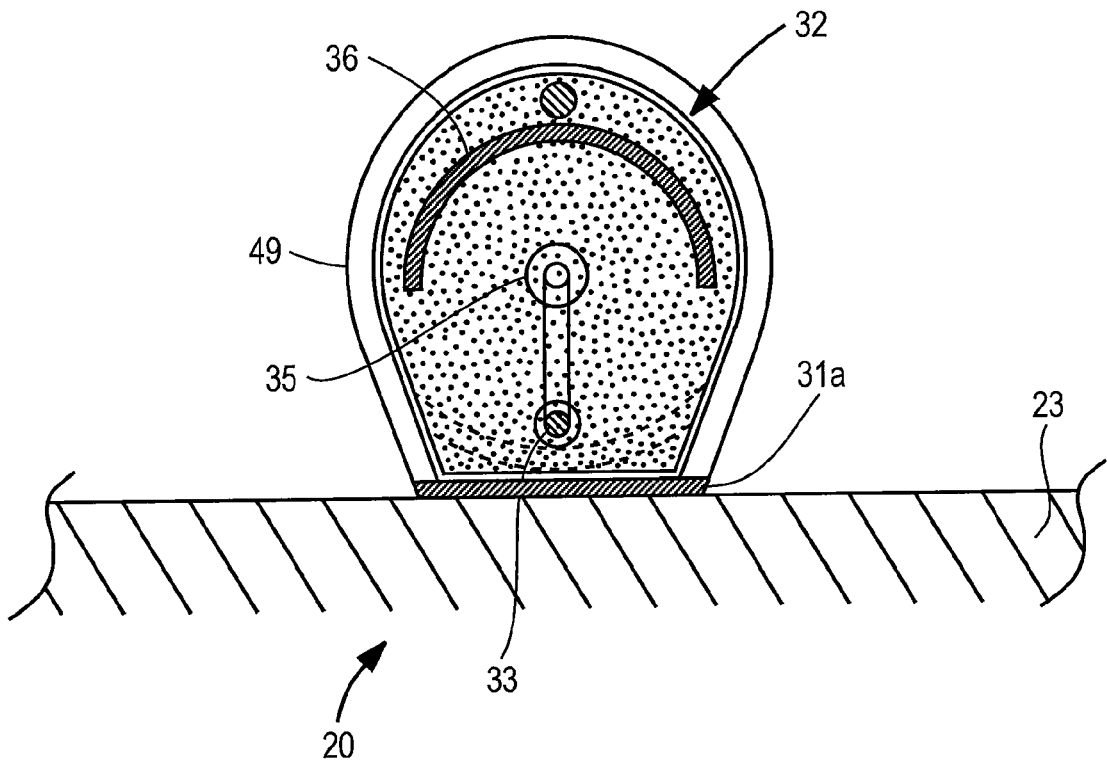
FIGS. 4A, 4B are cross sectional views of alternative embodiments of sensors according to the present invention.
Figure 4B:
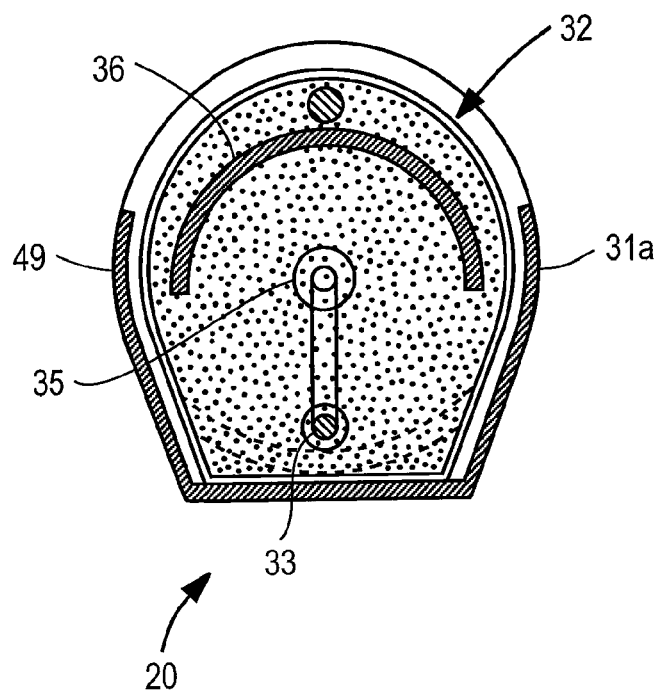

Turning now to the figures, a measurement or assessment instrument or device, generally designated 20 in FIGS. 4A, 4B, is provided to assess the transmurality of an ablation lesion 21 which extends from a first surface 22 of a targeted biological tissue 23 toward an opposed second surface 25 thereof. As will be described in greater detail below, these lesions are generally formed during surgical tissue ablation procedures through the application of tissue ablation instruments 26 (FIGS. 1-3 and 6). These tissue ablation instruments typically ablate tissue by directing ablative energy toward or into the target tissue 23 until a transmural ablation lesion is formed. The present invention, thus, evaluates the effectiveness, depth and completeness (i.e., the transmurality) of the ablation, an ablation made within cardiac tissue for example.

The measurement or assessment instrument 20 includes at least a first sensor 31a and at least a second sensor 31b. Sensor 31a is configured to engage the first surface 22 of the target tissue 23 and, while it can be place proximate or underneath a portion of the ablation instrument 26, sensor 31a is preferably operably attached to the ablation instrument 26. Sensor 31b is operably positioned proximate to the second surface 25 of tissue 23 and, more preferably, directly opposed to the ablation instrument 26. As will become more apparent with the discussion below, while the sensor 31b may be placed anywhere within a hollow organ, if the sensor 31b is placed in contact with the second tissue surface 25, placement opposing the instrument 26 is preferable as such placement improves measurement and analysis of the acquired tissue characteristic.

Sensor 31b is mounted upon an elongated shaft 40 for placement. As stated above, the sensor 31b can be placed anywhere within a hollow organ, the left ventricle of a heart for example. If it is desirable to place the sensor 31b in contact with the second tissue surface 25, the elongated shaft may be made malleable to allow for actively forcing the sensor 31b into contact with the tissue surface 25, or otherwise encouraging such placement. Additionally, the distal end of shaft 40 may be pointed to allow for piercing and advancing through the tissue 23. The shaft 40 is sized to allow the elastic and resilient epicardial surface to close the opening created when the shaft 40 is removed. Alternatively, the shaft may be placed into position through the use of a purse string opening, well known in the art.

As shown, sensor 31b may be an elongated electrode surrounding a distal portion of shaft 40. However, sensor 31b may alternatively comprise several sensors 31b1-bn along the distal portion of shaft 40 (not shown), each sensor 31b1-bn being selectively and operably attached to a data acquisition system, providing a more detailed analysis, as discussed in more detail below, of the propagation of the ablation lesion 21 through the tissue 23.

Placing the sensor 31b in contact with the second tissue surface 25 is advantageous since such placement displaces fluids or other materials which would interfere with creation of the lesion, cooling the tissue for example. Thermal isolation of the second tissue surface 25 may be enhanced by adapting shaft 40 to cover more tissue surface 25 area, isolating the tissue surface 25 from fluids such as blood flow, as generally depicted by arrow B. For example, the cross-sectional geometry of the distal shaft 40 may be rectangular, engaging more tissue and, thus, thermally isolating more tissue from fluids, such as blood.

Briefly, the present invention is suitable for use in connection with tissue ablation instruments adapted to ablate the biological tissue walls of internal organs and the like. These tissue walls typically have wall thickness from one surface of the tissue to an opposite surface of the tissue in the range of about 2 mm to about 10 mm. Thus, through direct contact with or exposure of the one surface of the tissue to an ablation assembly 32 of the ablation instrument 26, the formation of the ablation lesion generally propagates from the one surface toward the opposed second surface of the tissue. It will be understood, however, and as set forth below, that any modality of ablative energy may be applied.

As generally shown in FIG. 3, tissue ablation instruments 26 typically include a distal, ablation assembly 32 which emits ablative energy in a manner sufficient to cause tissue ablation. Thus, by manipulating and strategically placing the ablation assembly 32 adjacent to or in contact with the targeted biological tissue to be ablated, strategic lesion formation can occur. By way of example and as will be described in greater detail below, a series of strategically placed ablation lesions around heart collectively create a predetermined conduction pathway. More specifically, the conduction pathway is formed between a sinoatrial node and an atrioventricular node of the heart, such as required in the MAZE III procedure to treat arrthymias.

Any source of ablative energy may be employed to achieve ablation. These include, but are not limited to, Radio Frequency (RF), laser, cryogenic, ultrasound, one or more resistive heating elements, microwave, or any other energy which can be controllably deployed to ablate tissue. The source of ablation can also be one or a family of chemical agents. For example, localized ethanol injection can be used to produce the ablation lines. RF probes that apply an RF conduction current in the range of about 450 kHz to about 550 kHz. Typical of these RF ablation instruments include ring electrodes, coiled electrodes or saline electrodes. Another source of ablative energy are laser based energy sources sufficient to ablate tissue. These include $CO_2$ or Nd:YAG lasers which are transmitted to the ablation assembly 32 through fiber optic cable or the like. Yet another alternative energy source is cryogenic energy. These cryogenic probes typically apply a cryogenic fluid, such as a pressurized gas (e.g., Freon), through an inflow lumen to a decompression chamber in the ablation assembly. Upon decompression or expansion of the pressurized gas, the temperature of the ablation assembly is sufficiently reduced to cause tissue ablation upon contact therewith. The ablative energy may also be ultrasonically based. For example, one or a series of piezoelectric transducers may be provided as an ablative element which delivers acoustic waves sufficient to ablate tissue. Such transducers include piezoelectric materials such as quartz, barium oxides, etc. It should be noted that, in some cases, the sensors 31 may be an integral part of the ablating element itself, an RF electrode adapted to emit ablative energy there from for example.

One particularly effective source of ablative energy, however, is microwave energy which is emitted as an electromagnetic field by the ablation assembly. One advantage of microwave energy, as mentioned, is that the field is easier to control and safer than direct current applications. Typically, the microwave energy permeates the tissue to a depth proportional to the energy applied. The microwave probes, further, are capable of generating substantially larger and longer lesions than RF catheters, which greatly simplifies the actual ablation procedures. Moreover, recent advances in the antenna assembly designs enable even greater control of the field emission in predetermined directions for strategic lesion formation.

Briefly, referring back to FIG. 3, ablation instrument 26 is shown having an ablation assembly 32 adapted to ablate the targeted tissue. More specifically, the ablation assembly 32 generally includes an elongated antenna 33 coupled to a transmission line 35 for radially generating the electric field substantially along the longitudinal length thereof. To directionally control the radiation of ablative energy, a shield device 36 substantially shields a surrounding radial area of the antenna wire 33 from the electric field radially generated therefrom, while permitting a majority of the field to be directed generally in a predetermined direction. An insulator 37 is disposed between the shield device 36 and the antenna 33, and enables the transmission of the directed electric field in the predetermined direction. Also depicted in FIG. 3 is an exemplary placement of sensor 31a. As shown, sensor 31a is placed proximate to antenna 33, from which ablative energy is emitted.

Preferably, sensor electrodes 31 are provided by ring electrodes of various dimensions, as described herein. Such electrodes may be composed of a conductive or metallic material, such as silver, platinum or other biocompatible metals suitable for the purposes described herein. Non-metallic conductive electrodes like Ag—AgCl, or saline electrodes could also be used.

Each sensor 31a is coupled to a respective transmission line 42 to electrically transmit from a signal source or generator. In a similar fashion, each sensor 31b is coupled to a respective transmission line 42 to electrically transmit a signal from the second tissue surface 25 to a processing unit (not shown).

The outer surface of ablation instrument 26 may be grooved or defined with a plurality of annular slots 44 formed and dimensioned for receipt of the one or more sensors 31a therein. Preferably, the width and depth of each slot 44 is substantially similar to that of the respective sensor 31 so that it may be seated generally flush with the exterior surface of the instrument 26, and substantially free of gaps or spaces. This would facilitate placement of the ablation instrument 26 upon the tissue first surface 22.

Briefly turning also to FIGS. 4A-4B, alternative configurations of the one or more sensors 31a are shown. More specifically, while sensor 31a is shown as substantially cylindrical in FIG. 3, sensor 31a can be any suitable geometric shape consistent with the methods described herein. FIGS. 4A-4B depicts alternative cross-sectional geometries of sensor 31a. More specifically, FIG. 4A depicts the sensor 31a imbedded within an emission surface in contact with tissue 23. FIG. 4B, alternatively depicts a cross-sectional geometry substantially surrounding the periphery 49 of the assembly 32 portion of instrument 26. The configuration of FIG. 4B is advantageous since it ensures contact between the sensor 31a and irregular tissue surfaces. The longitudinal length of the one or more sensors 31a may be any suitable length for ensuring contact with the tissue, preferably between about 1 mm and about 5 mm.

The ablation instrument 26 includes a manipulating device 38 which cooperates with the ablation assembly 32 to orient the antenna and shield device in position to perform the desired ablation. This manipulating device 38, for example, may include a handle member or the like coupled to the ablation assembly, as shown in FIGS. 1-3 and 6. Another example of the manipulating device 38 includes a guide assembly 39 of FIG. 5, having a track system slideably receiving the ablation assembly 32. Such microwave ablation systems are described in the U.S. Pat. Nos. 6,245,062; 6,312,427 and 6,287,302 to Berube et al.; U.S. patent application Ser. No. 09/484,548 to Gauthier et al., filed Jan. 18, 2000, and entitled "MICROWAVE ABLATION INSTRUMENT WITH FLEXIBLE ANTENNA ASSEMBLY AND METHOD," and U.S. patent application Ser. No. 09/751,472 to Mody et al., filed Dec. 29, 2000, and entitled "A PREFORMED GUIDE APPARATUS WITH A SLIDING MICROWAVE ABLATION INSTRUMENT AND METHOD," each of which is incorporated herein by reference.

Briefly, when microwave energy is applied, the power supply (not shown) will include a microwave generator which may take any conventional form. The optimal frequencies are generally in the neighborhood of the optimal frequency for heating water. By way of example, frequencies in the range of approximately 800 MHz to 6 GHz work well. Currently, the frequencies that are approved by the Federal Communication Commission (FCC) for Industrial, Scientific and Medical work includes 915 MHz and 2.45 GHz and 5.8 GHz (ISM band). Therefore, a power supply having the capacity to generate microwave energy at frequencies in the neighborhood of 2.45 GHz may be chosen. A conventional magnetron of the type commonly used in microwave ovens is utilized as the generator. A solid-state amplifier could also be used. It should be appreciated, however, that any other suitable microwave power source (like a Klystron or a traveling-wave tube (TWT)) could be substituted in its place, and that the explained concepts may be applied at other frequencies like about 434 MHz, 915 MHz or 5.8 GHz (ISM band).

Figure 7A:
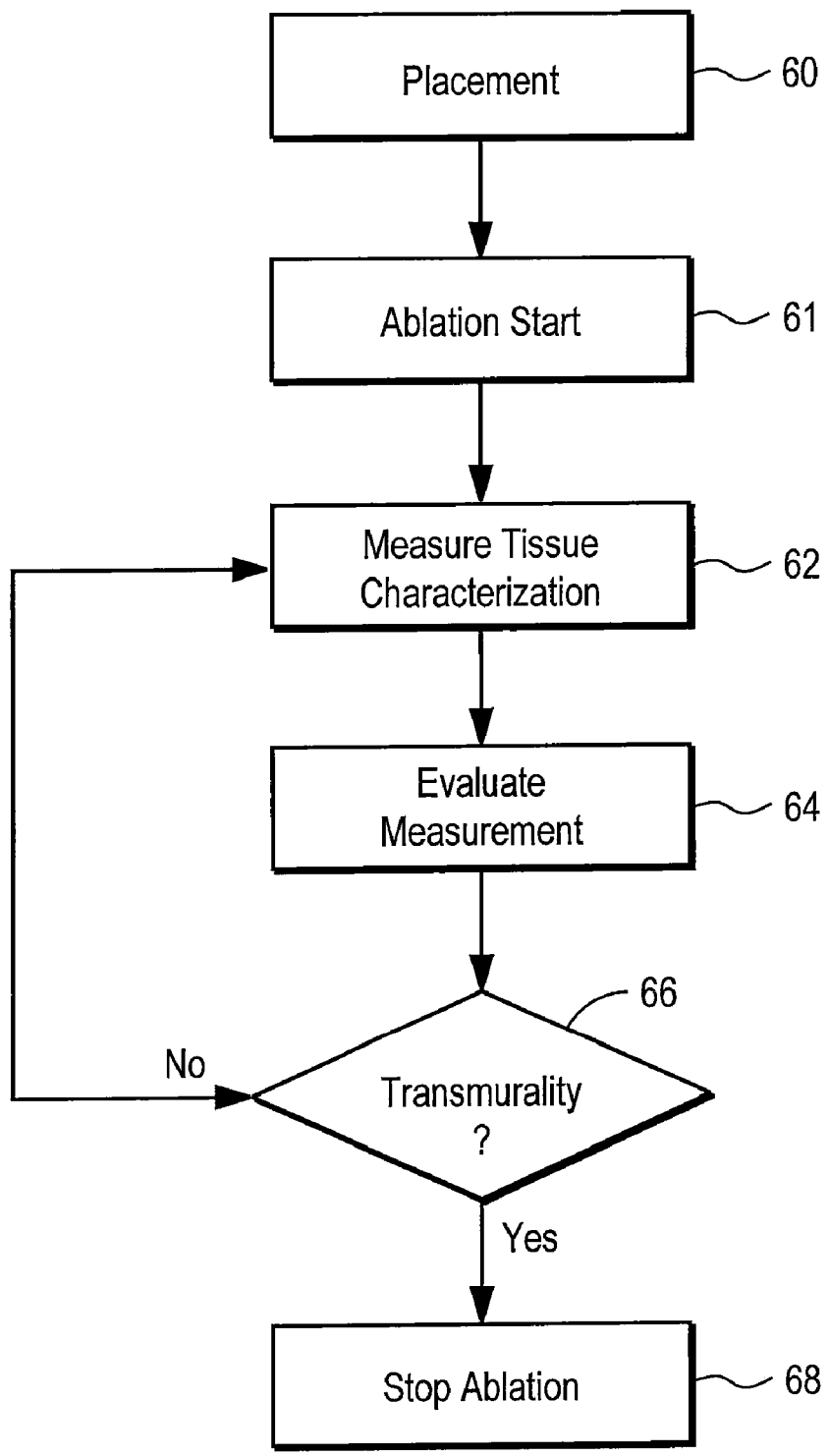
FIG. 7A is a flow chart depicting the steps of transmurality assessment in accordance with the present invention.
Figure 7B:
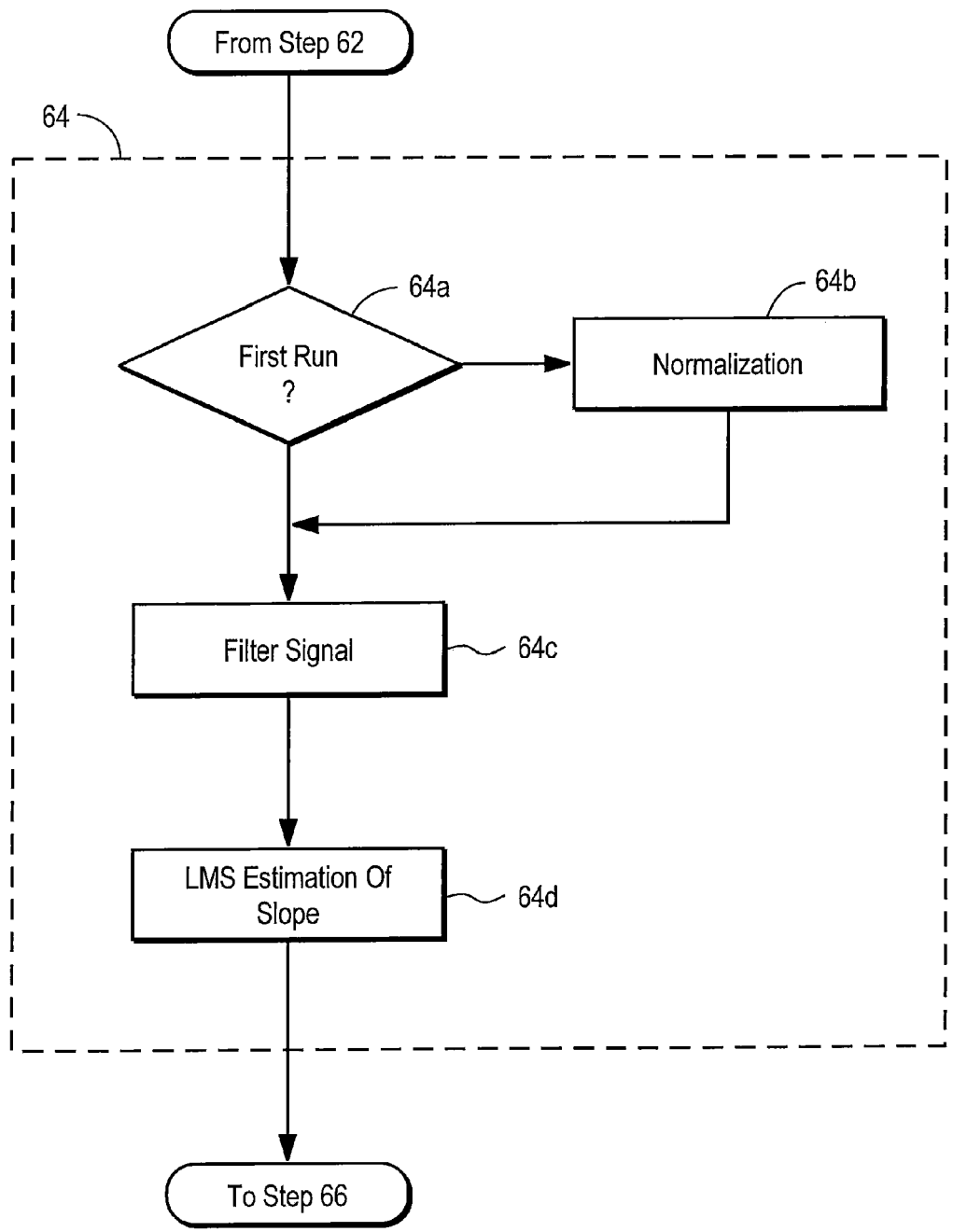
FIG. 7B is a flow chart depicting the steps of measurement evaluation in accordance with the present invention.

Turning also to FIGS. 7A and 7B, a general methodology of transmurality assessment conducted in accordance with the present invention will be described in greater detail. More specifically, FIG. 7A depicts a flow chart of steps to assess the progression of an ablation lesion through targeted tissue, ultimately determining when the lesion is transmural. In a first step 60, the ablation instrument 26 utilized for the ablation process is place proximate to or in contact with the first tissue surface 22, as required by the modality in use. At this time, the sensors 31a-b of the assessment instrument 20 are positioned relative to the target tissue, as described above. Once placement is complete the ablation process is initiated with the application of ablative energy directed toward the targeted tissue 23 in a step 61. The tissue characteristic is then measured and evaluated in steps 62 and 64, respectively. These measured characteristics are related to at least one of the conduction time, the conduction velocity, the phase angle, and the impedance of the targeted tissue. Based upon these measurements a transmural assessment is made in a step 66. If transmurality is not achieved, control is directed back to the tissue characteristic measurement step 62. However, if transmurality is achieved, the ablation process is stopped in a step 68. The steps of FIG. 7A may be performed by a User, a surgeon for example, or may be performed as part of a program executed by a central processing unit.

It is important to note that the transmural assessment procedure of FIG. 7A can be performed between sensor 31a and any other sensor 31n, various electrodes for example, as described herein. Moreover, as described in greater detail below, a plurality of electrodes 31a may be operably attached to the ablation instrument 26, each being able to be utilized, alone or in combination, with any other sensor 3 in to assess transmurality.

Now turning specifically to FIG. 7B, the step of evaluating the tissue characteristic measurement, in accordance with the present invention, will be discussed in greater detail. As discussed above, a tissue characteristic measurement is made in the step 62, the information acquired being passed on for evaluation in step 64. As shown, steps 64a-64d are subset steps of the step 64 depicted in FIG. 7A.

Generally, data is acquired over a period of time, thus, a number of data points will be collected and analyzed as part of the methods described herein. More specifically, a determination is made in a step 64a as to whether this is the first evaluation performed for a given ablation process, referred to herein as a first run. If this is a first run, a normalization of the acquired data is performed in a step 64b. Normalization is achieved through the initial acquisition of a plurality of data points over a period of time. In this way, future acquired data can be compared, or otherwise evaluated, with respect to this normalized value rather than an actual value. This is advantageous since it allows for evaluation of the tissue characteristic measurement as an overall trend, observing decreasing or increasing values for example. Data acquisition during normalization can involve conditioning and processing the data as described immediately below with respect to further steps as part of the evaluation procedure.

After normalization, the acquired data is conditioned in a filtering step 64c. The filtering acts to remove undesirable signals induced by transmitted signals, as discussed herein, by inconsistent contact between a sensor 31 and a tissue surface or by movements of sensors 31 within a chamber of a hollow organ related to physiological events, a heart beat for example. While the filtered signal resulting from the filtering step 64c may be utilized to provide a transmurality assessment determination, the value obtained may be processed further to enhance the assessment determination in a step 64d. As described herein, one parameter to observe is decreasing impedance during creation of an ablation lesion. While the current value of measured impedance can be compared with previous values to assess transmurality, estimation of the of the line representative of the measured impedance, using the least mean square calculation, may be determined and compared to a predetermined value, close to zero for example, providing an indication of transmurality. It should be apparent that certain analysis would require acquisition of numerous data points. In this case, a means for data storage and retrieval would be required.

Once the tissue measurement characteristic is evaluated in steps 64a-d, the evaluation is used as a basis, as stated above, to determine transmurality in step 66. Upon an indication of transmurality the ablation process is stopped in step 68. At this point, if more ablation lesions are desired as part of a long continuous lesion path, the ablation instrument 26 is moved to facilitate the creation of additional lesions. The assessment instrument 20 is placed as described herein and a new assessment is performed on the one or more additional lesions.

Figure 8:
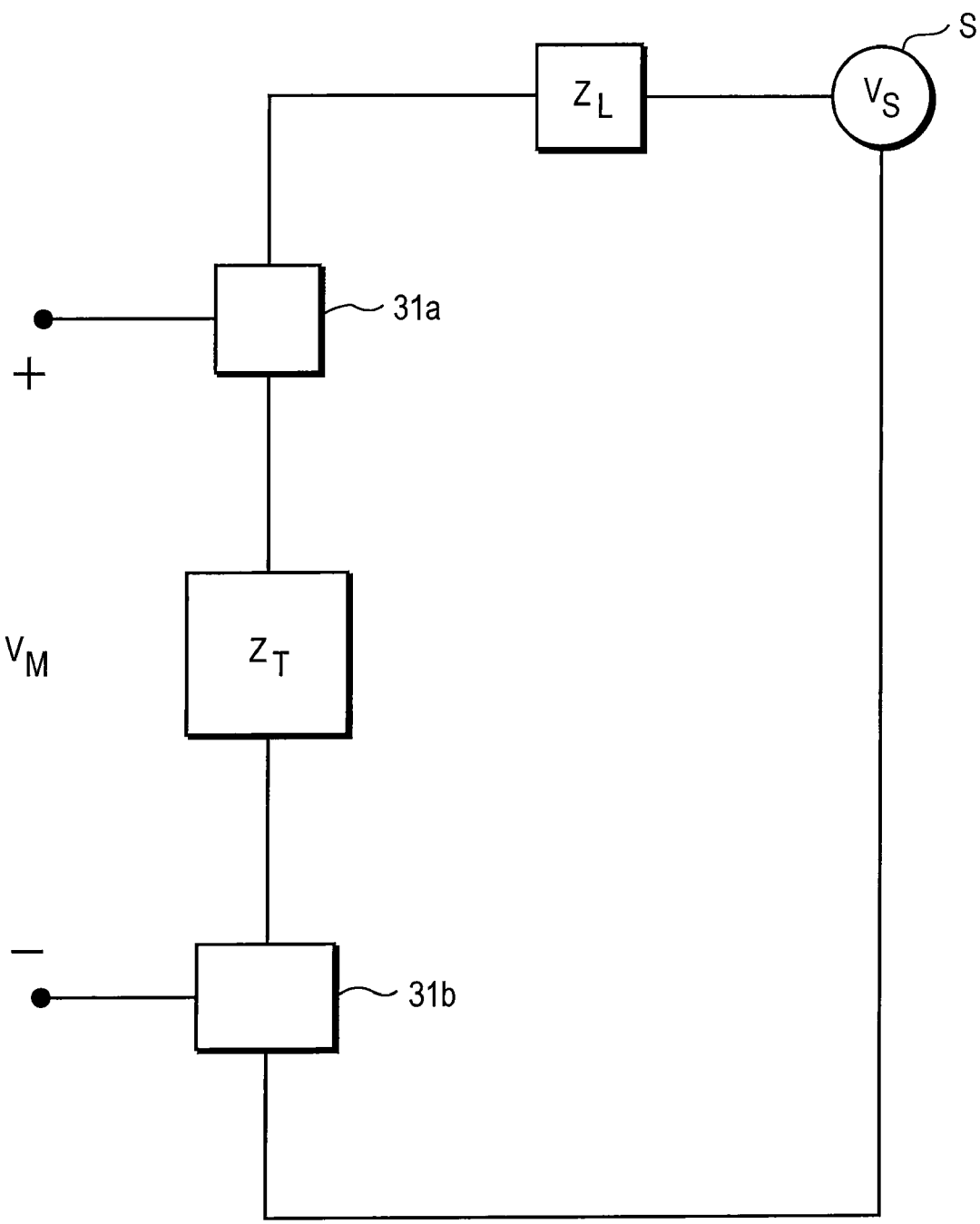
FIG. 8 is an exemplary equivalent electrical circuit used in the methods of transmurality assessment in accordance with the present invention.

Referring also to FIG. 8, an example tissue measurement setup will be described in greater detail. FIG. 8 depicts an exemplary setup for the measurement of tissue impedance through a portion of biological tissue between sensors, 31a and 31b in this example. As shown, a source S is electrically connected to sensor 31a. The source signal $V_s$ is applied to sensor 31a through a known load impedance $Z_L$. The source signal $V_s$ propagates through a portion of target tissue between sensors 31a and 31b, the target tissue having an impedance $Z_T$. During the step of measuring tissue impedance 62, the voltage difference $V_M$ between sensors 31a and 31b is measured. Since the impedances $Z_L$ and $Z_T$ form a simple voltage divider, the tissue impedance $Z_T$ can be calculated from the measured voltage $V_M$. Additionally, it should be noted that a phase angle related to the source signal and source current can also be calculated from this information, an increase in phase angle being indicative of increasing transmurality.

The impedance $Z_T$ measurement is then evaluated in the step 64. More specifically, as depicted in FIG. 1, as the ablation 21 propagates through the tissue 23, from sensor 31a toward sensor 31b, the impedance is observed to change with respect to previously obtained values, generally decreasing in value over time. Once the ablation propagates to the tissue second surface 25 of tissue 23, the impedance measured in step 62 between sensors 31a and sensor 31b, as compared with previous measurements, is observed to be constant.

It should be apparent that the determination of the 'constant measurement' may be predetermined as being something other than equal, with respect to previous measurements. For example, when the impedance change is noted to be within a certain limit, the change in value may be deemed constant. Additionally, the sampling time associated with the assessment loop steps 62, 64, and 66 may any suitable time, preferably to minimize the time in assessing transmurality. Alternatively, the assessment loop sampling time may be directly proportional to the acquired assessment value itself, the change in impedance for example. When a large change in value is observed, less sampling is required, and when there is a small change in value observed the sampling rate may be increased to better determine the exact time of transmurality.

Referring also to FIG. 1, it should be readily understood that the transmitted signals are selected, or otherwise defined, based upon the desired tissue measurement. For example, certain transmitted signals may be designed to passively interface with the tissue, while other signals may be designed to induce a response from the tissue itself. Passively, as used in the immediate discussion, means that the transmitted signals do not interfere with the normal rhythm of the heart.

For example, the two or more sensors 31 may be configured to passively measure the electrical impedance therebetween. This measurement can be made using any suitable method, simple utilization of a standard ohmmeter for example. However, as described in more detail above, the configuration of FIG. 8 is preferred.

The source signal $V_s$ may be any suitable passive voltage at a frequency of at least 100 khz, preferably five volts ac at a frequency of at least 100 khz, more preferably, at a frequency from about 400 khz to about 450 khz. It is important to note that the source may be selected to also carry out the ablation process as well as provide excitation for the tissue characteristic measurement. The signal generating source or power source S may be any suitable source providing the desired voltages at the desired frequencies, such as a standard function generator readily available from Hewlett-Packard Company of Palo Alto, Calif., for example.

Figure 2:
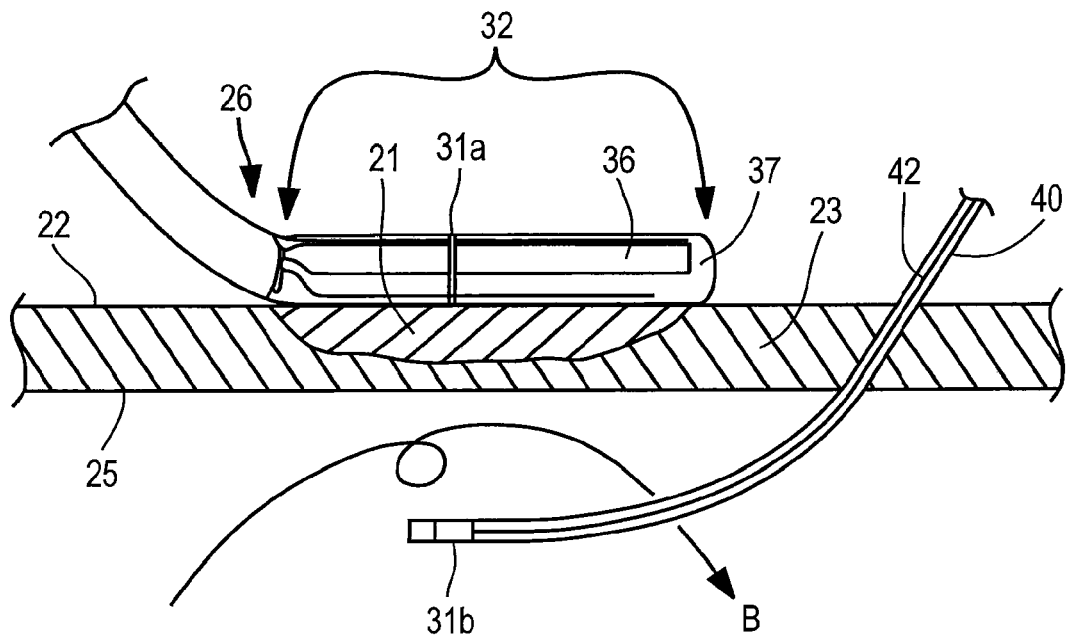
FIG. 2 is a fragmentary side elevation view, in cross-section, of an alternative embodiment of the transmurality assessment.

With reference now to FIG. 2, an alternative embodiment of the present invention will be discussed in greater detail. The embodiment of FIG. 2 is similar to the embodiment of FIG. 1, however the one or more sensors 31b mounted on a distal portion of shaft 40a are located within a chamber of an organ, surrounded by fluid. For example, in the left atrium of the heart, surrounded by blood circulating as depicted by arrow B. As with shaft 40, shaft 40a may be advanced through tissue 23 through any suitable means, a purse string for example. Alternatively, the distal tip of shaft 40a may be adapted to pierce and advance through tissue 23, the elastic nature of the epicardial surface closing the opening once the shaft 40a is removed.

With the electrode 31b positioned within a chamber of the heart, the blood provides a conductive median for acquisition of the voltage measurement $V_m$, as described above. Shaft 40a may be constructed from any suitable material consistent with the modality utilized during the ablation procedures and measurements made as part of the methods of transmurality assessment, as described herein. Shaft 40a may be flexible, malleable or bendable, or rigid. Perturbations created by oscillatory movement of shaft 40a relative the second tissue surface 25 may be filtered, as stated above.

Figure 5:
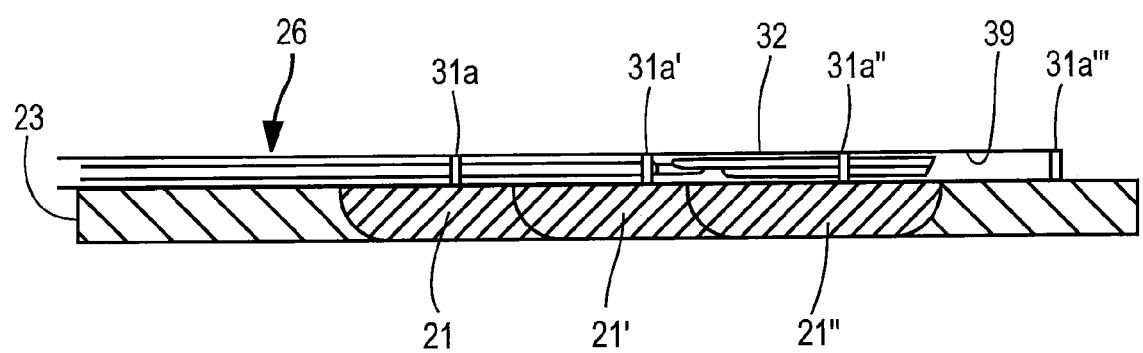
FIG. 5 is a fragmentary, top perspective view, partially cut-away, of another alternative embodiment of the transmurality assessment instrument of FIG. 3 mounted to a guide assembly for a sliding ablation assembly of an ablation instrument.

Now referring to FIG. 5, an ablation instrument 26 incorporating a guide assembly 39 is shown. The assembly 39 includes at least one lumen passing therethrough through which the antenna assembly 32 translates. As depicted, once the guide assembly 29 is placed upon the tissue 23, the antenna assembly is advance to a first position at which time a first ablation lesion 21 is created. Once lesion 21 is created, the antenna assembly 32 is translated to a second position at which time a second ablation lesion 21' is created and, in a similar manner, lesion 21" is created, resulting in a continuous lesion encompassing lesions 21, 21' and 21".

As shown, plurality of sensors 31a are mounted to the external surface of assembly 39 using any suitable means discussed herein, such as crimping, imbedding or epoxy bonding. At each lesion 21, 21', 21", a corresponding sensor 31a, 31a', 31a" assists with the transmurality assessment related to that lesion. Therefore, as should be readily understood, the plurality, of sensors 31a, 31a', 31a", may each be selectively connected to the signal source in order to assess transmurality for a particular lesion 21, 21', 21" in a manner as disclosed herein.

Figure 6:
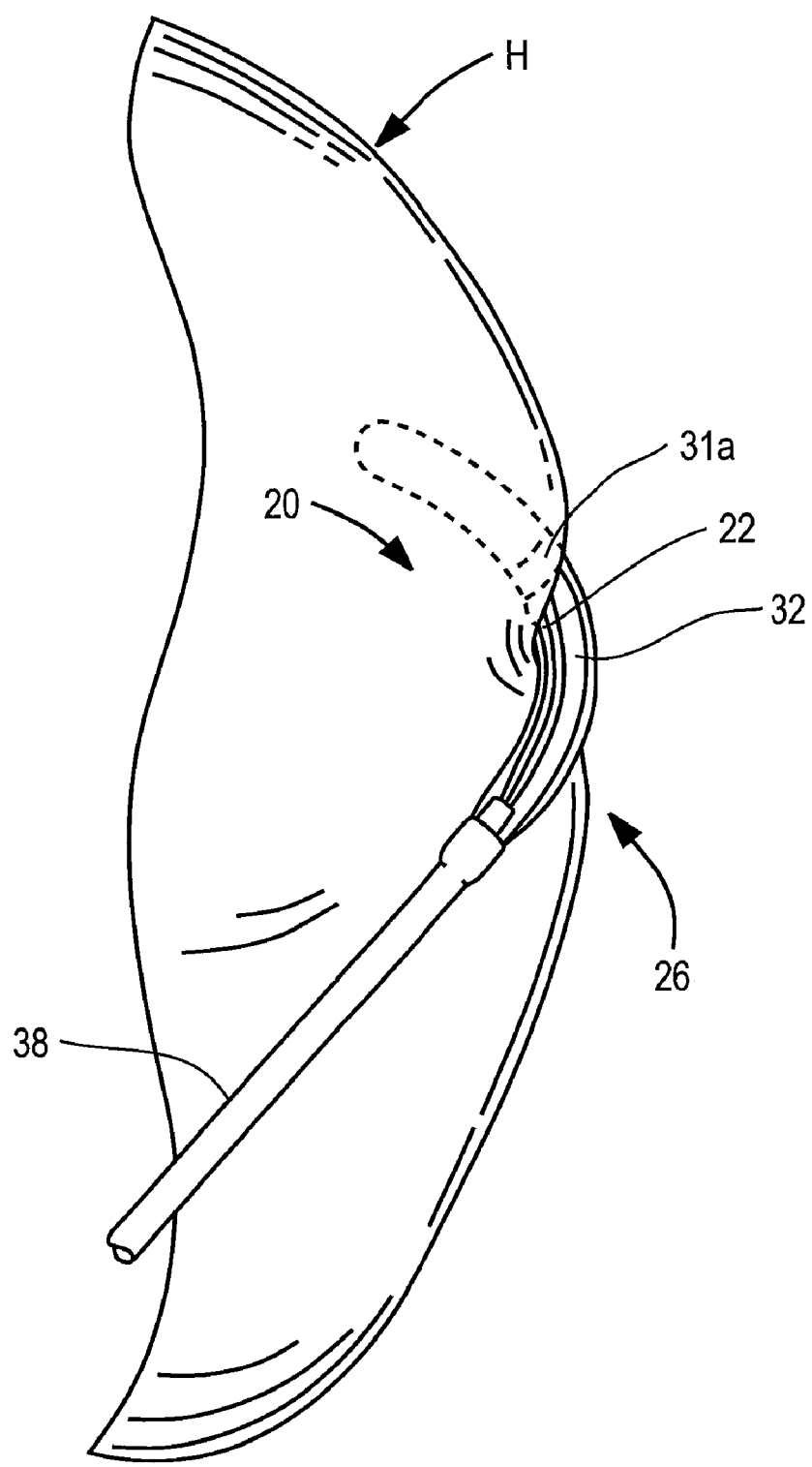
FIG. 6 is a top perspective view, in cross-section, of an ablation instrument with the transmurality assessment instrument of FIG. 1 engaged against cardiac tissue.

One significant application of the present invention is in the treatment of medically refractory atrial fibrillation of the heart. For example, as represented in FIG. 6, an ablation instrument 26 can be manipulated to position the ablation assembly 32 into engagement with or substantially adjacent to the epicardium or endocardium of the targeted cardiac tissue 23 of the heart H. Ablation energy, preferably an electromagnetic field, is generated from the ablation assembly 32 sufficiently strong to cause tissue ablation to form an elongated ablation lesion 21 extending from the first surface toward an opposed second surface 25 of the heart. As viewed in FIGS. 1-3, the sensor 31a is operably mounted to a distal portion of the instrument 26, along at least a portion of the instrument 26 from which the ablative energy is emitted. Once the instrument 26 is properly placed, the shaft 40a, having at least one sensor 31b operably mounted thereon is place in contact with the tissue second surface 25 or within a chamber of the heart H. These electrodes, as mentioned, are adapted to selectively transmit and receive electrical signals from one or more electrodes 31 to measure at least one of conduction time, conduction velocity, phase angle, and impedance through at least a portion of the targeted cardiac tissue. This data, of course, is applied to assess the progression and completeness of the created ablation lesion 21. To fully treat the medically refractory atrial fibrillation, the procedures are repeated (i.e., the manipulating, generating and transmitting or receiving) to form a plurality of strategically positioned ablation lesions and/or to divide the left and/or right atria to substantially prevent reentry circuits For instance, using this technique, the pulmonary veins may be electrically isolated from other tissues of the heart. In particular, the strategic positioning of the ablation lesions (not shown) cooperates to create a predetermined conduction pathway between a sinoatrial node and an atrioventricular node of the heart. Further, this procedure may be performed during open or minimally invasive surgical procedures. In the latter procedure, the heart may be beating or arrested.

What is claimed is:

1. Apparatus for assessing the transmurality of an ablation lesion formed in targeted biological tissue, the apparatus comprising:
an elongated guide assembly having disposed therein an instrument that radiates electrical ablative energy;
a first electrode disposed on an outer surface of the guide assembly for placement in contact with the ablation lesion in targeted biological tissue; and
a second electrode disposed on an elongated member configured for positioning thereof in contact with the biological tissue spaced from the first electrode;
a circuit coupled to said first and second electrodes and operable for transferring electrical signals therebetween through a portion of the targeted biological tissue; and
the instrument is disposed to translate within the guide assembly and radiate from within the guide assembly electrical ablative energy operatively separate from the electrical signals transferred by the first and second electrodes, for ablating tissue along a course aligned with the guide assembly.

2. Apparatus according to claim 1, wherein the first electrode is configured to contact the targeted tissue at a first surface location thereon and the second electrode is configured to contact the targeted tissue at a second surface location spaced from the first surface location on the targeted tissue.

3. Apparatus according to claim 1 comprising:
an additional electrode disposed on the outer surface of the guide assembly spaced from the first and second electrodes for placement in contact with the targeted biological tissue,
each of the first, second and additional electrodes being individually selectable for transfer of electrical signals through targeted biological tissue to measure at least one of conduction time, conduction velocity, phase angle, and impedance through at least a portion of targeted biological tissue disposed near a selected electrode.

4. Apparatus according to claim 1, wherein the first electrode is adapted to transmit a first signal in the targeted tissue and the second electrode is adapted to receive a signal from the targeted tissue responsive to the first signal.

5. Apparatus according to claim 1 in which the elongated member supporting the second electrode is configured for operably positioning the second electrode within the interior of an organ.

6. Apparatus according to claim 5, wherein a distal tip of the elongated member is adapted to pierce and pass through tissue.

7. Apparatus according to claim 1, comprising a plurality of spaced apart first electrodes operably attached to an outer surface of the guide assembly.

8. Apparatus according to claim 1 in which the first electrode and the circuit coupled thereto supply to targeted tissue in contact therewith a high frequency electric signal distinct from the radiated electrical ablative energy;
the second electrode and the circuit coupled thereto receive from within targeted tissue in contact therewith the high frequency signal supplied by the first electrode, said circuit analyzing the applied and received high frequency signals relative to at least one of conduction time, conduction velocity, phase angle and impedance for assessing transmurality of an ablation lesion in targeted tissue in contact with the first and second electrodes.

* * * * *